United States Patent
Samain et al.

(10) Patent No.: US 11,178,955 B2
(45) Date of Patent: Nov. 23, 2021

(54) TRANSFER DEVICE AND PROCESS FOR MAKING UP KERATIN MATERIALS

(71) Applicant: L'OREAL, Paris (FR)

(72) Inventors: Henri Samain, Bievres (FR); Franck Giron, Lagny sur Marne (FR)

(73) Assignee: L'OREAL, Paris (FR)

( * ) Notice: Subject to any disclaimer, the term of this patent is extended or adjusted under 35 U.S.C. 154(b) by 430 days.

(21) Appl. No.: 15/108,302

(22) PCT Filed: Dec. 19, 2014

(86) PCT No.: PCT/IB2014/067133
§ 371 (c)(1),
(2) Date: Jun. 26, 2016

(87) PCT Pub. No.: WO2015/097615
PCT Pub. Date: Jul. 2, 2015

(65) Prior Publication Data
US 2016/0316891 A1 Nov. 3, 2016

(30) Foreign Application Priority Data

Dec. 27, 2013 (FR) .................................. 1363632

(51) Int. Cl.
*A45D 40/30* (2006.01)
*B44C 1/17* (2006.01)
(Continued)

(52) U.S. Cl.
CPC ............ *A45D 40/30* (2013.01); *A45D 34/04* (2013.01); *A61K 8/0204* (2013.01);
(Continued)

(58) Field of Classification Search
CPC .................... A45D 40/30; A45D 34/04; A45D 2200/1036; A61K 8/02; A61K 8/04;
(Continued)

(56) References Cited

U.S. PATENT DOCUMENTS

| 2,746,460 A | 5/1956 | Jellinek |
| 4,137,180 A | 1/1979 | Naik et al. |

(Continued)

FOREIGN PATENT DOCUMENTS

| CN | 1476319 A | 2/2004 |
| CN | 1519278 A | 8/2004 |

(Continued)

OTHER PUBLICATIONS

Office Action dated Sep. 10, 2018 in Japanese Patent Application No. 2016-542897 (7 pages).

(Continued)

*Primary Examiner* — Rachel R Steitz
(74) *Attorney, Agent, or Firm* — Shumaker, Loop & Kendrick, LLP

(57) ABSTRACT

Process for making up an area of human keratin materials using a makeup device including a substrate having at least one transfer surface, and a coat of cosmetic colouring ink borne by the transfer surface and obtained by printing, using at least one digital printer, and a cosmetic coating comprising an oil borne by the transfer surface. The cosmetic coating is at least partially superposed on the coat of ink and laying above and/or below the coat of ink, and the process includes the step of simultaneously transferring onto the area to be made up all or part of the coat of ink and all or part of the coating superposed thereon.

17 Claims, 1 Drawing Sheet

(51) Int. Cl.

| | | |
|---|---|---|
| *A61Q 1/02* | (2006.01) | |
| *A45D 34/04* | (2006.01) | |
| *A61K 8/891* | (2006.01) | |
| *A61K 8/02* | (2006.01) | |
| *A61Q 1/04* | (2006.01) | |
| *A61Q 1/06* | (2006.01) | |
| *A61Q 19/00* | (2006.01) | |

(52) U.S. Cl.
CPC ............ *A61K 8/0233* (2013.01); *A61K 8/891* (2013.01); *A61Q 1/02* (2013.01); *A61Q 1/025* (2013.01); *A61Q 1/04* (2013.01); *A61Q 1/06* (2013.01); *A61Q 19/00* (2013.01); *B44C 1/1733* (2013.01); *A45D 2200/1036* (2013.01); *A61K 2800/87* (2013.01); *A61K 2800/872* (2013.01); *A61K 2800/874* (2013.01)

(58) Field of Classification Search
CPC .. A61K 8/0233; A61K 8/891; A61K 2800/87; A61K 2800/872; A61K 2800/874; A61Q 1/02; A61Q 1/025; A61Q 1/04; A61Q 1/06; A61Q 19/00; B44C 1/1733
See application file for complete search history.

(56) References Cited

U.S. PATENT DOCUMENTS

| | | |
|---|---|---|
| 4,804,719 A | 2/1989 | Weaver et al. |
| 4,874,554 A | 10/1989 | Lange et al. |
| 4,903,840 A | 2/1990 | So |
| 4,925,667 A | 5/1990 | Fellows et al. |
| 4,936,325 A | 6/1990 | Davis |
| 4,999,418 A | 3/1991 | Krutak et al. |
| 5,030,708 A | 7/1991 | Krutak et al. |
| 5,032,670 A | 7/1991 | Parham et al. |
| 5,043,376 A | 8/1991 | Sharma et al. |
| 5,047,084 A | 9/1991 | Miller et al. |
| 5,078,160 A | 1/1992 | Carbonnier |
| 5,102,980 A | 4/1992 | Krutak et al. |
| 5,104,913 A | 4/1992 | Sharma et al. |
| 5,106,942 A | 4/1992 | Krutak et al. |
| 5,194,463 A | 3/1993 | Krutak et al. |
| 5,281,659 A | 1/1994 | Weaver et al. |
| 5,396,913 A | 3/1995 | Wallschlaeger |
| 5,421,765 A | 6/1995 | Lehmann et al. |
| 5,913,315 A | 6/1999 | Todd |
| 5,958,560 A | 9/1999 | Ewan |
| 5,997,134 A | 12/1999 | Hotomi et al. |
| 5,997,136 A | 12/1999 | Fujisawa et al. |
| 6,013,248 A | 1/2000 | Luebbe et al. |
| 6,106,852 A | 8/2000 | Vineberg |
| 6,168,656 B1 | 1/2001 | Schulz et al. |
| 6,190,730 B1 | 2/2001 | Matsos |
| 6,299,967 B1 | 10/2001 | Collins et al. |
| 6,312,124 B1 | 11/2001 | Desormeaux |
| 6,342,094 B1 | 1/2002 | Kabalnov |
| 6,367,484 B1 | 4/2002 | Ramin et al. |
| 6,428,164 B1 | 8/2002 | Missell et al. |
| 6,543,893 B2 | 4/2003 | Desormeaux |
| 6,622,733 B2 | 9/2003 | Saksa |
| 6,626,183 B1 | 9/2003 | Pietrocola et al. |
| 7,241,503 B2 | 7/2007 | Noguchi |
| 7,648,364 B2 | 1/2010 | Dauga et al. |
| 8,007,062 B2 | 8/2011 | Edgar et al. |
| 8,083,422 B1 | 12/2011 | Simmons |
| 8,545,613 B2 | 10/2013 | Blette |
| 8,695,610 B2 | 4/2014 | Samain et al. |
| 9,616,668 B1 | 4/2017 | Rabe |
| 2002/0020422 A1 | 2/2002 | Iosilevich |
| 2002/0035182 A1 | 3/2002 | L'Alloret et al. |
| 2002/0061321 A1 | 5/2002 | Bara |
| 2002/0110672 A1 | 8/2002 | Muratore-Pallatino et al. |
| 2002/0155069 A1 | 10/2002 | Pruche |
| 2002/0164295 A1 | 11/2002 | Scavone et al. |
| 2003/0053976 A1 | 3/2003 | Tournilhac et al. |
| 2004/0057742 A1 | 3/2004 | Richtsmeier |
| 2004/0078278 A1 | 4/2004 | Dauga |
| 2004/0241423 A1 | 12/2004 | Ramin et al. |
| 2004/0246327 A1 | 12/2004 | Elzi |
| 2005/0148908 A1 | 7/2005 | Stover |
| 2006/0093943 A1 | 5/2006 | Hyo et al. |
| 2006/0098076 A1 | 5/2006 | Liang |
| 2006/0150994 A1 | 7/2006 | Pilmanis |
| 2007/0144634 A1 | 6/2007 | Hitchcock |
| 2008/0031836 A1 | 2/2008 | Ilekti |
| 2008/0053476 A1* | 3/2008 | LaHood ................. A45D 33/38 132/320 |
| 2008/0152681 A1* | 6/2008 | Brown ..................... B82Y 5/00 424/401 |
| 2008/0176160 A1 | 7/2008 | Deprez et al. |
| 2009/0325221 A1 | 12/2009 | Long et al. |
| 2010/0031834 A1 | 2/2010 | Morgavi et al. |
| 2010/0068247 A1 | 3/2010 | Mou et al. |
| 2010/0086693 A1 | 4/2010 | Yamada et al. |
| 2011/0020023 A1 | 1/2011 | Hirai |
| 2011/0025040 A1 | 2/2011 | Dominguez |
| 2011/0123703 A1 | 5/2011 | Mohammadi et al. |
| 2011/0141188 A1 | 6/2011 | Morita |
| 2011/0159463 A1 | 6/2011 | Samain |
| 2011/0164263 A1 | 7/2011 | Samain et al. |
| 2011/0268873 A1 | 11/2011 | Blette |
| 2012/0027423 A1 | 2/2012 | Kawai |
| 2012/0027443 A1 | 2/2012 | Kawai |
| 2012/0029417 A1 | 2/2012 | Samain et al. |
| 2012/0064011 A1 | 3/2012 | Schumann |
| 2012/0192884 A1 | 8/2012 | Nasu et al. |
| 2012/0244316 A1* | 9/2012 | Dobler ................... A61M 35/00 428/141 |
| 2012/0244465 A1 | 9/2012 | Kobayashi |
| 2012/0307304 A1 | 12/2012 | Moreno |
| 2013/0216295 A1 | 8/2013 | Wong |
| 2014/0233967 A1 | 8/2014 | Suzuki |
| 2015/0053759 A1 | 2/2015 | Cahill et al. |
| 2015/0150767 A1 | 6/2015 | Klug et al. |
| 2016/0000208 A1 | 1/2016 | Wong |
| 2016/0103962 A1 | 4/2016 | Costantino et al. |
| 2016/0316890 A1 | 11/2016 | Samain |
| 2016/0316892 A1 | 11/2016 | Giron |
| 2016/0317403 A1 | 11/2016 | Giron |
| 2016/0324298 A1 | 11/2016 | Samain |
| 2016/0324299 A1 | 11/2016 | Samain |
| 2019/0133300 A1 | 5/2019 | Hedglin |

FOREIGN PATENT DOCUMENTS

| | | |
|---|---|---|
| CN | 101018064 A | 8/2007 |
| CN | 101056605 A | 10/2007 |
| CN | 101686927 A | 3/2010 |
| CN | 101980694 A | 2/2011 |
| CN | 102490540 A | 6/2012 |
| DE | 102005050123 A1 | 4/2007 |
| EP | 705593 A1 | 4/1996 |
| EP | 0728460 A1 | 8/1996 |
| EP | 0749746 A1 | 12/1996 |
| EP | 0749747 A1 | 12/1996 |
| EP | 780114 A1 | 6/1997 |
| EP | 0923928 A1 | 6/1999 |
| EP | 0930060 A1 | 7/1999 |
| EP | 0938887 A1 | 9/1999 |
| EP | 1000607 A1 | 5/2000 |
| EP | 1048282 A1 | 11/2000 |
| EP | 1059047 A1 | 12/2000 |
| EP | 1304056 A2 | 4/2003 |
| EP | 1925278 A1 | 5/2008 |
| EP | 2090935 A1 | 8/2009 |
| FR | 2232303 A1 | 1/1975 |
| FR | 2759941 A1 | 8/1998 |
| FR | 2792192 A1 | 10/2000 |
| FR | 2858226 A1 | 2/2005 |
| FR | 2900594 A | 8/2007 |
| FR | 2905630 A1 | 3/2008 |
| FR | 2909844 A1 | 6/2008 |
| FR | 2939033 A1 | 6/2010 |

(56) References Cited

FOREIGN PATENT DOCUMENTS

| | | | |
|---|---|---|---|
| JP | S62180000 A | 8/1987 |
| JP | S63-188616 A | 8/1988 |
| JP | H-2503065 A | 9/1990 |
| JP | H04-208997 A | 7/1992 |
| JP | H11-007203 A | 1/1999 |
| JP | H11-169231 A | 6/1999 |
| JP | H-11169231 A | 6/1999 |
| JP | H11169231 A | 6/1999 |
| JP | H11-346828 A | 12/1999 |
| JP | 2001-245945 A | 9/2001 |
| JP | 2001278739 A | 10/2001 |
| JP | 3266197 B2 | 1/2002 |
| JP | 2002-058528 A | 2/2002 |
| JP | 2002068935 A | 3/2002 |
| JP | 2002-148998 A | 5/2002 |
| JP | 2003006452 A | 1/2003 |
| JP | 2004501177 A | 1/2004 |
| JP | 2004262913 A | 9/2004 |
| JP | 2005040356 A | 2/2005 |
| JP | 2005-088434 A | 4/2005 |
| JP | 2007204487 A | 8/2007 |
| JP | 2008-127388 A | 6/2008 |
| JP | 2010505843 A | 2/2010 |
| JP | 2010-186133 A | 8/2010 |
| JP | 2012-002869 A | 1/2012 |
| JP | 2012502908 A | 2/2012 |
| JP | 2012072081 A | 4/2012 |
| JP | 2012-518457 A | 8/2012 |
| JP | 2012518457 A | 8/2012 |
| JP | 2012-520837 A | 9/2012 |
| JP | 2012249849 A | 12/2012 |
| JP | 2013-031504 A | 2/2013 |
| JP | 2013137758 A | 7/2013 |
| JP | 2013532003 A | 8/2013 |
| JP | 2013-252709 A | 12/2013 |
| WO | 1992007913 A1 | 5/1992 |
| WO | 9848659 A1 | 11/1998 |
| WO | 02/36083 A1 | 5/2002 |
| WO | 03033270 A1 | 4/2003 |
| WO | 2006/128737 A1 | 12/2006 |
| WO | 2006128737 A1 | 12/2006 |
| WO | 2007/134171 A1 | 11/2007 |
| WO | 2010/004526 A1 | 1/2010 |
| WO | 2010004526 A1 | 1/2010 |
| WO | 2010004531 A1 | 1/2010 |
| WO | 2010/095118 A | 8/2010 |
| WO | 2010/105842 A2 | 9/2010 |
| WO | 2012081065 A1 | 6/2012 |
| WO | 2013093889 A2 | 6/2013 |
| WO | 2013126513 A1 | 8/2013 |
| WO | 2013178701 A2 | 12/2013 |

OTHER PUBLICATIONS

Office Action dated Sep. 27, 2018 in U.S. Appl. No. 15/108,292 (16 pages).
Pubchem; castor oil—https://pubchem.ncbi.nlm.nih.gov/compound/castor_oil#section=Top; 1 page; 2010.
Final Rejection for U.S. Appl. No. 15/108,076 dated Aug. 21, 2017.
Canon, fix your own printer, https://www.fixyourownprinter.com/posts/66407 (dated: Mar. 17, 2010) (1 page).
Office Action dated May 18, 2018 for Chinese Patent Application No. 2014800713416 (22 pages).
Office Action for JP App. No. 2016-543072 dated Dec. 17, 2018 with English Translation(7 pages).
Office Action for JP App. No. 2016-543056 dated Dec. 17, 2018 with English Translation (7 pages).
Office Action for JP App. No. 2016-543027 dated Dec. 21, 2018 with English Translation (13 pages).
Office Action for JP App. No. 2016-543057 dated Dec. 17, 2018 with English Translation (14 pages).
Non-Final Office Action for U.S. Appl. No. 15/108,292 dated Jul. 7, 2017.
Restriction Requirement for U.S. Appl. No. 15/108,303 dated Sep. 6, 2017 (7 pages).
Office Action issued in Chinese Application No. 201480071272.9 dated Jul. 2, 2018 (14 pp).
Office Action issued in U.S. Appl. No. 15/108,295 dated Aug. 6, 2018 (56 pp).
Office Action issued in U.S. Appl. No. 15/108,151 dated Aug. 7, 2018 (60 pp).
Chinese Office Action dated Dec. 5, 2018 in Chinese Application No. 201480071307.9 (8 pages).
Japanese Office Action dated Nov. 19, 2018 for Japanese Application No. 2016-542996 (32 pages).
LA Colors 30 Eye Design Palettes—Review, Dyno Pretty Pup, http://dynopupbeauty.blogspot.nl/2012/03/la-colors-30-eye-design-palettes-review.html, Mar. 16, 2012 (5 pages).
Notice of Allowance dated Nov. 13, 2018 issued in U.S. Appl. No. 15/108,303 (27 pages).
Non-Final Office Action in U.S. Appl. No. 15/108,192 dated Oct. 6, 2017 (6 pages).
International Search Report for PCT/IB2014/067133 dated Mar. 11, 2015 (5 pages).
Dyno Pretty Pup: "Dyno Pretty Pup Beauty Diary: LA Colors 30 Eye Design Palettes—Review." Mar. 16, 2012 (4 pages).
Written Opinion for PCT/IB2014/067133 (4 pages).
First Office Action for CN Pat. Appln. No. 201480076509.2 with English Translation dated Oct. 30, 2017, 9 pages.
Final Rejection for U.S. Appl. No. 16/108,292 dated Jan. 30, 2018, 21 pages.
International Search Report for PCT/IB2014/067130 dated Mar. 11, 2015 (5 pages).
International Search Report for PCT/IB2014/067132 dated Apr. 28, 2015 (4 pages).
International Search Report for PCT/IB2014/067134 dated Apr. 24, 2015 (4 pages).
International Search Report for PCT/IB2014/067136 dated Jul. 7, 2015 (5 pages).
International Search Report for PCT/IB2014/067138 dated Mar. 11, 2015 (3 pages).
Apr. 12, 2018 Office Action issued in U.S. Appl. No. 15/108,303.
Office Action dated Jul. 2, 2018 issued in Japanese Patent Application No. 2016-543073 (17pp).
Office Action dated Jun. 5, 2018 issued in Chinese Patent Application No. 201480074439.7 (16 pp).
Restriction and Election of Species Requirement in U.S. Appl. No. 15/108,292 dated Mar. 1, 2017 (8 pages).
Non-Final Office Action in U.S. Appl. No. 15/108,076 dated Mar. 16, 2017 (12 pages).
"Papilio Laser Printable Temporary Tattoo Paper" (http://www.papilio.com/laser temporary tattoo paper.html), Dec. 14, 2013 (3 pages).
"Cheap laser printer paper for toner transfer?" (http://www.fountainpennetwork.com/forum/topic/41250-cheap-laser-printer-paper-for-toner-transfer/), Oct. 2, 2007 (11 pages).
Office Action dated Apr. 23, 2018 in European Patent Application No. 14 833 256.2.
Final Rejection for U.S. Appl. No. 15/108, 292 dated Apr. 26, 2019 (7 pages).
Non-Final Office Action for U.S. Appl. No. 15/108,295 dated Jun. 6, 2019 (12 pages).
Final Rejection for U.S. Appl. No. 15/108,295 dated Feb. 5, 2019 (10 pages).
Restriction Requirement for U.S. Appl. No. 15/108,305 dated Jan. 31, 2019 (8 pages).
English Translation of JP Office Action for JP Pat. App. No. 2016-542995 drafted Jan. 16, 2019 and dated Jan. 21, 2019 (3 pages).
Non-Final Office Action for U.S. Appl. No. 15/108,294 dated Mar. 4, 2019 (11 pgs.).
Final Rejection for U.S. Appl. No. 15/108,151 dated May 20, 2019 (11 pages).
Non-Final Office Action for U.S. Appl. No. 15/108,305 dated May 15, 2019 (17 pages).

(56) References Cited

OTHER PUBLICATIONS

Notice of Allowance for U.S. Appl. No. 15/108,294 dated Jul. 25, 2019 (9 pages).
Japanese Office Action for JP Pat. Appln. No. 2016-543057 dated Aug. 26, 2019 (8 pages).
Notice of Allowance for U.S. Appl. No. 15/108,292 dated Aug. 29, 2019 (16 pages).
Japanese Office Action for JP Pat. Appln. No. 2016-543056 dated Aug. 26, 2019 (8 pages).
Japanese Office Action for JP Pat. Appln. No. 2016-542996 dated Sep. 2, 2019 (14 pages).
Japanese Office Action for JP Pat. Appln. No. 2016-542897, dated Sep. 17, 2019 (10 pages).
Non-Final Office Action for U.S. Appl. No. 15/108,151 dated Feb. 25, 2021 (8 pages).
Final Rejection for U.S. Appl. No. 15/108,295 dated Jun. 15, 2020 (12 pages total).
Final Rejection for U.S. Appl. No. 15/108,151 dated Oct. 23, 2020 (8 pages).
Non-Final Office Action for U.S. Appl. No. 15/108,305, dated Jan. 6, 2021 (14 pgs.).
Restriction Requirement for U.S. Appl. No. 16/694,035, dated Jan. 12, 2021 (8 pgs.).
Advisory Action for U.S. Appl. No. 15/108,151, dated Jan. 8, 2021 (3 pgs.).
Non-Final Office Action for U.S. Appl. No. 15/108,151 dated Jul. 20, 2020 (10 pages).
Final Rejection for U.S. Appl. No. 15/108,295 dated Apr. 2, 2021 (18 pages).
Non-Final Office Action for U.S. Appl. No. 15/108,295 dated Jan. 31, 2020 (14 pages).
Office Action for Korean Patent App. No. 10-2016-7020078 dated Jan. 27, 2021 with English Translation (14 pages).
Final Rejection for U.S. Appl. No. 15/108,305, dated Mar. 3, 2020 (24 pages).
Japanese Office Action for JP Patent App. No. 2016-543072 dated Mar. 12, 2020 with English translation (7 pages).
Japanese Office Action for 2019-127617 dated Jun. 22, 2020 with English Translation (9 pages).
Non-Final Office Action for U.S. Appl. No. 15/108,295 dated (15 pages).
Final Rejection for U.S. Appl. No. 15/108,305 dated Jun. 15, 2021 (15 pages).
Non-Final Office Action for U.S. Appl. No. 16/694,035 dated May 10, 2021 (7 pages).
Korean Office Action for KR Pat. Appln. No. 10-2016-7020687, dated Feb. 25, 2021 with English Translation (22 pages).
Supplemental Notice of Allowance for U.S. Appl. No. 15/108,295 dated Aug. 11, 2021 (6 pages).
Notice of Allowance for U.S. Appl. No. 15/108,295, dated Aug. 5, 2021 (10 pages).
European Office Action for EP Pat. Appln. No. 14833254.7 dated Aug. 30, 2021 (5 pages).
Non-Final Office Action for U.S. Appl. No. 15/108,151 dated Sep. 15, 2021 (10 pages).
Japanese Office Action for JP Pat. Appln. No. 2019-127617, drafted Aug. 12, 2021 and dated Sep. 6, 2021 with English Translation (11 pages).
Notice of Allowance for U.S. Appl. No. 15/108,305, dated Sep. 30, 2021 (13 pages).
Final Rejection issued for U.S. Appl. No. 16/694,035, dated Oct. 1, 2021 (11 pages).

\* cited by examiner

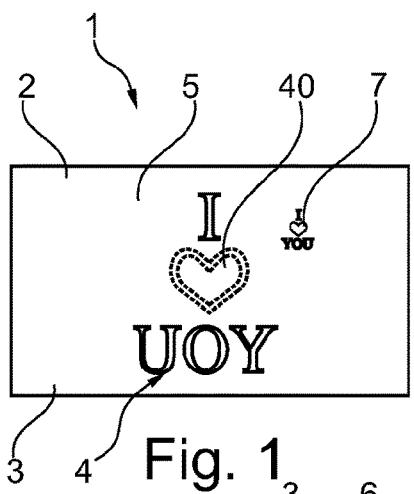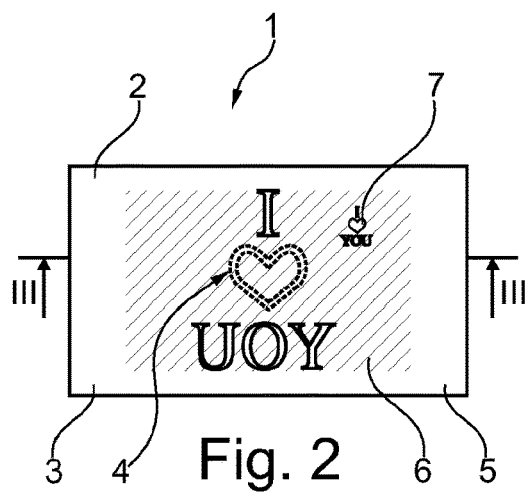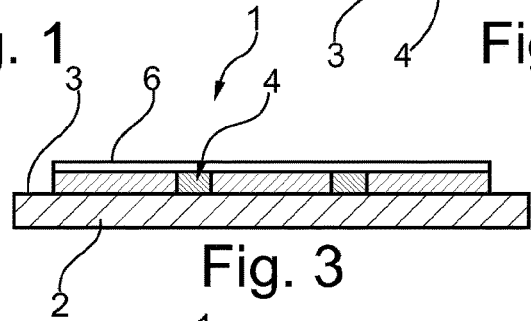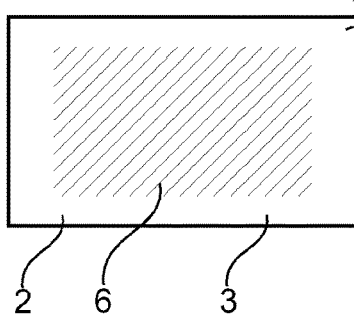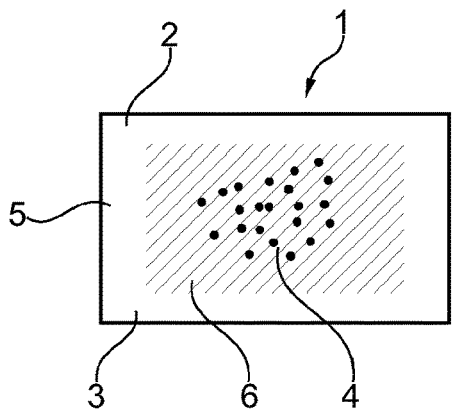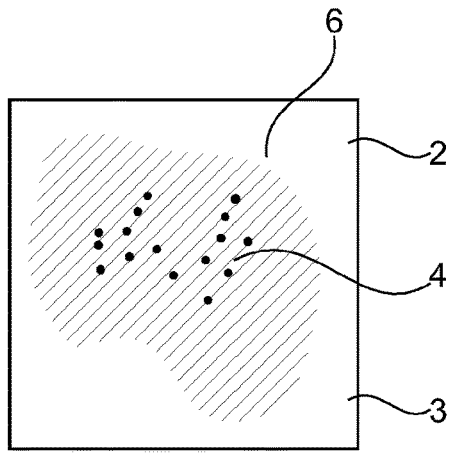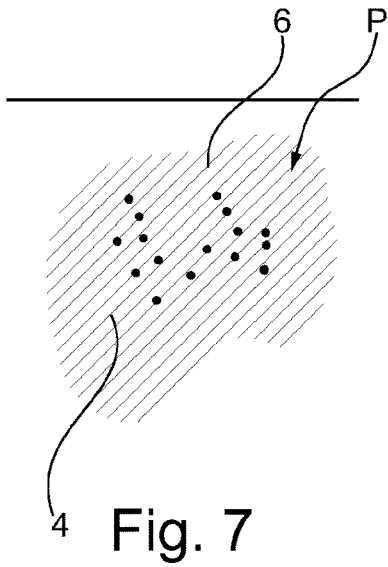

TRANSFER DEVICE AND PROCESS FOR MAKING UP KERATIN MATERIALS

BACKGROUND

There is a need to cover keratin materials, especially the skin and the lips, with precise coatings, such as patterns, on the millimetre scale.

However, no practical and efficient method exists. Drawing a pattern takes a long time to do and requires the intervention of a professional makeup artist. Methods using a patch or a decal transfer are disappointing, since the number of patterns is limited and it is difficult to avoid folds in the support bearing the pattern. This technique is, in particular, unsuitable for the face. On account of the movements of the facial skin, the support becomes cracked, thus giving a degraded and unaesthetic visual result.

There is a need for makeup patterns intended to cover a small area or indeed the entire area of the face or the lips.

There is a need to propose to each user a wide variety of patterns, colours, shapes and distributions, or even to propose to the user to define his patterns, so as best to satisfy his particular request, without the need to have a large number of references at hand.

Moreover, if the area to be made up has imperfections such as marks, microreliefs, wrinkles or fine lines, the makeup pattern has a less aesthetic result, not giving it a sharp, clean appearance.

There is a need for a makeup that is suited to the particular characteristics of the area of keratin materials to be treated. Thus, the makeup must occasionally be produced using a very thin coat of cosmetic ink to be comfortable for the user to wear, for example in the case of lip makeup.

There is a need to prepare the area to be made up so that the transfer keeps its precision completely intact and to have a beautiful, sharp and precise appearance.

The present invention is directed toward meeting all or some of these needs.

SUMMARY

According to a first of its aspects, the present invention relates to a process for making up an area of human keratin materials using a makeup device comprising:
- a substrate having at least one transfer surface, and
- a coat of cosmetic colouring ink borne by the transfer surface and obtained by printing, using at least one digital printer, and
- a cosmetic coating comprising an oil, the cosmetic coating being borne by the transfer surface, the cosmetic coating being at least partially superposed on the coat of ink and laying above and/or below the coat of ink,
the process comprising the step of simultaneously transferring onto the area to be made up all or part of the coat of ink and all or part of the coating superposed thereon.

The term "human keratin materials" denotes the skin, including the scalp, the lips, the nails, the hair, the eyelashes and the eyebrows; preferably the skin.

The term "digital printer" means a machine for printing in the form of pixels using digital data, different from a machine comprising a printing form. The use of at least one coat of cosmetic ink obtained by printing using a digital printer advantageously makes it possible to obtain great precision for a complex and customizable makeup.

The colouring ink and the coating deposited are intended to be placed in contact simultaneously with the keratin materials so as to obtain, by transfer, a makeup result on the keratin materials.

The process of the invention is easy to perform and allows transfer in a single gesture with good relative positioning of the pattern and the coating, avoiding pattern shifts.

The makeup effect obtained is very interesting. The keratin materials, especially the skin, are coated with a coating and it is also possible to see at least one pattern that is precise.

The invention allows makeup application that combines a standard colouring cosmetic composition with a customizable pattern. The invention also makes it possible to integrate the composition, especially a foundation, and the pattern, which allows a certain level of discretion, if so desired. Good precision of the pattern is maintained, by means of printing, without it being impaired by the coating composition.

The invention also makes it possible to make up areas of the skin by smoothing these areas to improve their visual aspect.

The presence of the coating also improves the visual rendering of the patterns, over the entire made-up area, without allowing the skin defects to show through.

According to another aspect, the invention also relates to a process for manufacturing a transfer device for making up human keratin materials, comprising a substrate having at least one transfer surface, this process comprising the following steps:
- printing at least one coat of at least one cosmetic colouring ink on the transfer surface using at least one digital printer,
- applying at least one cosmetic composition to the transfer surface to form a coating, the cosmetic coating being at least partially superposed on the coat of ink, the coat of colouring ink and the cosmetic coating being intended to be transferred simultaneously onto the keratin materials so as to obtain a makeup result on the keratin materials.

The printing of the coat of ink may be performed on the transfer surface already partly covered with the coating.

The coating may at least partly be produced after printing the coat of ink onto the transfer surface.

In one embodiment example, the colouring ink is printed in a predefined pattern, the process comprising a step of choosing and/or making the pattern by a user and of transmitting, by means of a machine connected to at least one printer that performs the printing, information relating to this pattern.

The machine may be a computer, an advanced portable telephone, also known as a "smartphone", or a tablet computer. The machine may be connected physically and/or by means of a data exchange network to the said printer.

The printer may be an inkjet printer, for example a thermal or piezoelectric printer, a sublimation printer or a laser printer.

In one example, the printer is a laser printer arranged to allow the formation by electrophotography or magnetophotography of a coat of ink having a pattern on a transfer surface using at least one cosmetic toner and to deliver the toner present on the transfer surface in a state that is sufficiently free to allow it to be taken up or transferred by contact with the human keratin materials.

The term "cosmetic toner" should be understood as meaning a pulverulent cosmetic composition that is compatible with the formation of an image via an electrophotographic or magnetophotographic process as used in laser printers. Preferably, it is a toner that is suitable for electrophotographic use.

The toner is cosmetic in the sense that it is compatible with an application to human keratin materials. Depending on the surface to be made up, the formulation of the toner may be different. For example, for an application to the hair or the nails, it is possible to use certain compounds that might not be used for an application to the lips, for example.

The printer may be a food-grade inkjet printer such as the Gatocopy A426 machine allowing printing onto non-flat objects.

In one embodiment example, the printing is performed directly onto a non-flat transfer surface, corresponding especially to the outer surface of a roller.

The printing may use several different inks, especially inks of different colours.

The printing may use at least three, especially at least four, five, six, seven, eight, nine, ten, eleven or twelve colouring inks of different colours.

The printing may use only colouring inks that produce primary colours. As a variant, the printing may use both colouring inks that produce primary colours and at least one colouring ink that produces a non-primary colour.

The printing of the colouring ink may be three-colour or four-colour printing.

The pattern obtained by printing may comprise several areas of different colours. As a variant, the pattern obtained by printing is a flat tint.

The colouring ink may be deposited in several printing passes. In other words, a first fraction of the colouring ink may first be printed onto the transfer surface, followed by a second fraction of the colouring ink on all or part of the first fraction.

The printing of the coat of ink may be performed on the transfer surface already covered with the coating.

The printing may be performed on a dry or non-dry coating. One variant consists in depositing a coating of a composition onto a transfer surface, waiting for it to dry and then printing.

In one variant, the coating is produced after printing the coat of ink onto the transfer surface.

The transfer step by placing the transfer surface in contact with the area to be made up is performed, for example, by exerting a pressure on the surface of the substrate opposite the transfer surface.

A process according to the invention may also comprise a step consisting in moving the transfer surface away from the area of the human keratin materials after the coat of ink and the coating have been transferred.

In one embodiment example, the coat of colouring ink is printed onto the transfer surface and then at least partly covered with a coating.

In one variant, the transfer surface is at least partly coated with a first coating, the coating comprising, for example, a pigment and/or a dye.

The coat of ink is then printed onto the first coating.

A composition may then be applied to form a second cosmetic coating.

Advantageously, the colouring ink is not entirely dry on the substrate when it is applied to the keratin materials. The colouring ink may be in fluid form when it is applied to the keratin materials.

All or part of the colouring ink borne by the transfer surface may be applied by transfer to the keratin materials.

In one embodiment example, at least 25%, especially 50%, especially 75% and especially substantially all of the colouring ink initially present on the transfer surface is applied by transfer to the keratin materials, preferably without addition of an intermediary fluid compound.

In one embodiment example, the application of the colouring ink is performed by application with pressure of the transfer surface onto the keratin materials.

The simultaneous transfer of the colouring ink and of the coating composition onto the area to be treated may be performed without rubbing.

Advantageously, the area of keratin materials intended to receive the colouring ink has not been pretreated at the time of the simultaneous transfer of the colouring ink and of the coating composition.

According to another aspect, the present invention relates to a transfer device for making up human keratin materials, comprising:
  a substrate having at least one transfer surface,
  a coat of cosmetic colouring ink borne by the transfer surface and obtained by printing, using at least one digital printer, and
  a cosmetic coating comprising an oil borne by the transfer surface,
the cosmetic coating laying above or below the coat of ink,
  at least partially superposed on the coat of ink,
the colouring ink and the cosmetic coating being intended to
  be applied to the keratin materials, especially by being placed in contact with the keratin materials, so as to obtain, by transfer, a makeup result on the keratin materials.

Substrate and Transfer Surface

In one embodiment example, the substrate of the makeup device according to the invention comprises at least one translucent or transparent area.

The translucent or transparent area allows a user to see through the substrate and thus to visualize more easily the surface to be made up before transferring the colouring ink. The presence of a translucent or transparent area thus advantageously contributes towards facilitating the production of a precise makeup result on the keratin materials.

The translucent or transparent area of the substrate can be totally or partly superposed with the coat of colouring ink, and especially may overlap it.

The coat of colouring ink may be superposed in its entirety on the translucent or transparent area of the substrate. As a variant, only part of the coat of colouring ink is superposed on the transparent area of the substrate.

The substrate may be made of a transparent or translucent material. In this case, the translucent or transparent area extends over the entire surface of the substrate.

As a variant, the substrate is opaque over all or part of its surface.

The substrate may be a flexible sheet or a rigid plate. It may be made of plastic (for example polyethylene or polystyrene). It may be woven or nonwoven. It may be made of organic or mineral material. It may be an aluminium foil.

The transfer surface of the substrate may be defined by all or part of: the outer surface of an applicator roller, the surface of an applicator pad, an element in sheet form, a patch, the surface of a porous foam, especially a sponge, a wipe, a coarse brush, a fine brush or a flocked tip.

The transfer surface is defined, for example, by all or part of the surface of a deformable sheet mounted on the surface of an applicator roller.

The transfer surface may retain the colouring ink by capillary action.

The transfer surface may be planar or nonplanar.

The transfer surface may be elastically deformable. Thus, in a first configuration, the transfer surface may be flat, and, in a second configuration, the transfer surface may be incurved, for example so as to take the shape of the keratin materials to be made up.

In one embodiment example, the transfer surface is detachable from a part of the substrate.

As will be detailed below, the substrate may be configured so that the transfer surface takes a first form, for example substantially flat, during printing, and a second form, different from the first, during the application of the colouring ink to the keratin materials.

The second form advantageously corresponds to the form of the surface of the keratin materials intended to be coated with the colouring ink, for example the form of a part of the face.

In one embodiment example, the substrate comprises an indication regarding the nature of the keratin materials intended to be made up with the colouring ink. This indication may be printed with the same ink or otherwise as that intended to be transferred.

The substrate is preferentially based on a non-absorbent material, for example a plastic film. The substrate is advantageously non-porous, at least on the face intended to receive the print.

In one embodiment example, when the colouring ink is intended to be applied to the cheeks and/or the nails, the substrate may have a thickness of greater than or equal to 1 mm, especially 3 mm, for example ranging from 1 to 5 mm.

In one embodiment example, when the colouring ink is intended to be applied to the area around the eyes and/or to the lips, the substrate may have a thickness of greater than or equal to 3 mm, especially 1 cm, for example ranging from 3 mm to 20 mm.

In one embodiment example, when the colouring ink is intended to be applied to the nose and/or in the area of the ears, the substrate may have a thickness of greater than or equal to 1 cm, especially 3 cm, for example ranging from 1 to 4 cm.

Thus, the substrate advantageously has a thickness adapted to the area of keratin materials to be made up.

The thickness of the substrate corresponds to its maximum dimension measured perpendicular to the transfer surface.

The substrate may be reusable. For example, printing is performed on the substrate, which is accessible for the transfer, but does not leave the printer. Thus, after use, the printer can reintegrate the substrate, clean it and make it ready for a new print.

Colouring Ink

The ink borne by the transfer surface preferably comprises a dyestuff.

Dyestuff

The dyestuff may comprise one or more dyes as described below.

The dyestuff may be present in the ink in a mass content ranging from 0.01% to 60%, preferably ranging from 0.1% to 40%, or even from 0.1% to 30% and preferentially ranging from 0.5% to 20%, relative to the total mass of the ink.

The colouring ink may comprise one or more dyestuffs chosen from water-soluble dyes, liposoluble dyes, pulverulent dyestuffs such as pigments, especially nacres, and glitter flakes, or alternatively colouring polymers.

The term "pigments" should be understood as meaning white or coloured, mineral or organic particles of any form, which are insoluble in the cosmetic medium, and which are intended to colour the cosmetic ink.

The term "nacres" should be understood as meaning iridescent particles of any form, in particular produced by certain molluscs in their shell, or else synthesized.

The pigments may be white, black or coloured, and mineral and/or organic. Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminium powder and copper powder.

Among the organic pigments that may be mentioned are carbon black, pigments of D&C type and lakes based on cochineal carmine or on barium, strontium, calcium or aluminium.

The nacreous pigments may be chosen from white nacreous pigments such as mica coated with titanium or with bismuth oxychloride, coloured nacreous pigments such as titanium mica coated with iron oxides, titanium mica coated especially with ferric blue or with chromium oxide, titanium mica coated with an organic pigment and also nacreous pigments based on bismuth oxychloride.

Among the water-soluble dyes, mention may be made of the disodium salt of ponceau, the disodium salt of alizarin green, quinoline yellow, the trisodium salt of amaranth, the disodium salt of tartrazine, the monosodium salt of rhodamine, the disodium salt of fuchsin, xanthophyll and methylene blue.

Among the liposoluble dyes, mention may be made of Sudan Red III (CTFA: D&C Red 17), lutein, quinizarine green (CTFA: D&C Green 6), alizurol purple SS (CTFA: D&C Violet 2), Sudan brown, D&C yellow 11, D&C Orange 5, quinoline yellow, curcumin, carotenoid derivatives such as lycopene, beta-carotene, bixin or capsanthin, and mixtures thereof. The dyeing polymers are generally copolymers based on at least two different monomers, at least one of which is a monomeric organic dye. Such polymeric dyes are known to those skilled in the art. Reference may be made, for example, to the following documents: U.S. Pat. No. 5,032,670; 4,999,418; 5,106,942; 5,030,708; 5,102,980; 5,043,376; 5,104,913; 5,281,659; 5,194,463; 4,804,719; WO 92/07913 or EP 1 048 282.

The printing may use several different inks, especially inks of different colours.

The printing may use at least three, especially at least four, five, six, seven, eight, nine, ten, eleven or twelve cosmetic inks of different colours.

The pattern formed by the colouring ink borne by the transfer surface may be coloured when observed under white light in the visible region (400 nm-800 nm). As a variant, the pattern is colourless under white light in the visible region, but may appear coloured when submitted to a chemical and/or energy stimulus, such as exposure to UV (365 nm-400 nm), for example when the colouring ink contains a photochromic or fluorescent dyestuff and/or dihydroxyacetone (DHA).

The printing may use only colouring inks that produce primary colours. As a variant, the printing may use both colouring inks that produce primary colours and at least one ink that produces a non-primary colour.

In one variant, the printing may use colouring inks that produce black and/or white.

The printing of the ink may be three-colour or four-colour printing.

The pattern obtained by printing may comprise several areas of different colours. As a variant, the pattern obtained by printing is a flat tint.

The pattern formed by the cosmetic ink printed on the transfer surface may be of any type.

Advantageously, the pattern may reproduce the appearance of relief and/or colour heterogeneities of the skin, for example freckles or a mole.

The coat of colouring ink may comprise several inks.

The colouring inks deposited by printing may be deposited onto the transfer surface in the form of dots and/or of raster lines, so as to form a half-tone image, for example a monochromatic or polychromatic image.

The coat of colouring ink may comprise several colouring inks of different colours, each deposited in dots.

Advantageously, the colouring ink is not entirely dry on the substrate when it is applied to the keratin materials. The colouring ink may be in fluid form when it is applied to the keratin materials.

All or part of the colouring ink borne by the transfer surface may be applied by transfer to the keratin materials.

In one embodiment example, at least 25% by mass, especially 50%, especially 75% and especially substantially all of the coat of colouring ink initially present on the transfer surface is applied by transfer to the keratin materials.

In one embodiment example, the application of the colouring ink is performed by application with pressure of the transfer surface onto the keratin materials.

The dyestuff may comprise one or more dyes, in particular acid dyes and/or colouring polymers, and/or one or more pigments, the pigments possibly being charged with dyes.

In one embodiment example, the dyestuff comprises one or more colouring agents that may be revealed under the action of an energy and/or chemical stimulus, for example photochromic compounds and/or dihydroxyacetone (DHA).

Preferably, the colouring ink present on the device is not entirely dry.

The application of a colouring ink that is not entirely dry onto the keratin materials facilitates the transfer of the ink.

The colouring ink may be in fluid form when borne by the transfer surface and before application to the keratin materials.

Advantageously, the fluid colouring ink has a viscosity ranging from 1 to 30 mPa·s, at 25° C.

The viscosity of an ink of the invention may be measured according to any process known to those skilled in the art, and especially according to the following conventional process. At 25° C. using a Rheomat 180 viscometer, equipped with a spindle rotating at 200 rpm, a person skilled in the art can select the spindle for measuring the viscosity from the spindles M1, M2, M3 and M4 on the basis of his general knowledge, so as to be able to perform the measurement.

When the ink is in the form of a cosmetic toner, this toner may comprise, besides a colouring agent, a compound for controlling the electrical charge, a particular additional filler, a lubricant, a wax and/or a binder.

Preferably, the particles of the toner have a mean size of between 1 and 16 μm. The toner comprises, for example, pigments with a particle size of between 1 and 10 μm.

Measurement of the Ability of the Colouring Ink to Transfer without the Need to Add an Intermediary Fluid Compound As mentioned above, the colouring ink is, particularly preferably, capable of transferring onto the keratin materials without the addition of an intermediary fluid compound.

To check whether a given colouring ink has this property, the coat of colouring ink under consideration borne by a surface is placed in contact with a sample of artificial skin sold by the company Beaulax under the brand name Bioskin ref #white 061031-2.

The contact is performed for a time of 1 s by applying a pressure of 5000 pascals (i.e. 50 g/cm$^2$) under atmospheric temperature and pressure conditions (20° C. and 1 bar). No intermediary fluid compound is added either to the colouring ink or to the sample before or during the contact.

A visual evaluation is performed.

If the colouring ink transfers onto the keratin materials, then the colouring ink is considered as being capable of transferring onto the keratin materials without the addition of an intermediary fluid compound.

Coating

The coating preferably comprises an oil.

The coating may be prepared by applying one or more coats, each of identical or different composition.

The coating may be colourless or coloured.

The composition may be in a fluid form.

The composition may be in the form of an oily gel or an emulsion.

The composition may be in a solid form.

According to the invention, the term "composition in solid form" means a composition which has a hardness such that it does not flow under its own weight, as opposed to "fluid" compositions. Such a composition may especially be in the form of a compact powder or in the form of a cast product.

The composition may be in emulsion form, in particular in the form of an oil-in-water or water-in-oil emulsion. The composition may be anhydrous. The term "anhydrous composition" means a composition containing less than 2% by weight of water, or even less than 0.5% of water, and is especially free of water. Where appropriate, such small amounts of water may especially be introduced by ingredients of the composition that may contain residual amounts thereof.

The composition may be a makeup and/or care composition.

The composition may be chosen from certain makeup compositions such as foundations, eyeshadows, face powders, lip glosses or lipsticks.

The composition may be chosen from skincare and lipcare compositions.

The oil present in the composition may be chosen from volatile and non-volatile oils of hydrocarbon-based, silicone or fluoro type. Preferably, the oil is a non-volatile oil.

The term "non-volatile oil" means an oil that remains on the skin at room temperature and atmospheric pressure for at least several hours, and that especially has a vapour pressure of less than 1.33 Pa (0.01 mmHg).

The term "hydrocarbon-based oil" means an oil mainly containing hydrogen and carbon atoms and optionally oxygen or nitrogen atoms.

Non-volatile hydrocarbon-based oils that may especially be mentioned include:

hydrocarbon-based oils of animal origin, hydrocarbon-based oils of plant origin such as triglycerides consisting of fatty acid esters of glycerol, the fatty acids of which may have chain lengths varying from $C_4$ to $C_{24}$, these chains possibly being linear or branched, and saturated or unsaturated; these oils are especially heptanoic or octanoic acid triglycerides, or alternatively wheatgerm oil, sunflower oil, grapeseed oil, sesame seed oil, corn oil, apricot oil, castor oil, shea oil, avocado oil, olive oil, soybean oil, sweet almond oil, palm oil, rapeseed oil, cottonseed oil, hazelnut oil, macadamia oil, jojoba oil, alfalfa oil, poppy oil, pumpkin oil, marrow oil, blackcurrant oil, evening primrose oil, millet oil, barley oil, quinoa oil, rye oil, safflower oil, candlenut oil, passion-flower oil and musk rose oil; shea butter; or else caprylic/capric acid triglycerides, for instance those sold by the company Stéarineries Dubois or those sold under the names Miglyol 810®, 812® and 818® by the company Dynamit Nobel, synthetic ethers containing from 10 to 40 carbon atoms;

linear or branched hydrocarbons of mineral or synthetic origin, such as petroleum jelly, polydecenes, hydrogenated polyisobutene such as Parleam®, squalane and liquid paraffins, and mixtures thereof, synthetic esters such as oils of formula $R_1COOR_2$ in which $R_1$ represents a linear or branched fatty acid residue containing from 1 to 40 carbon atoms and $R_2$ represents an, in particular, branched hydrocarbon-based chain containing from 1 to 40 carbon atoms, on condition that $R_1+R_2 \geq 10$, for instance purcellin oil (cetostearyl octanoate), isopropyl myristate, isopropyl palmitate, $C_{12}$ to $C_{15}$ alkyl benzoates, hexyl laurate, diisopropyl adipate, isononyl isononanoate, 2-ethylhexyl palmitate, isostearyl isostearate, 2-hexyldecyl laurate, 2-octyldecyl palmitate, 2-octyldodecyl myristate, alkyl or polyalkyl heptanoates, octanoates, decanoates or ricinoleates such as propylene glycol dioctanoate; hydroxylated esters such as isostearyl lactate, diisostearyl malate and 2-octyldodecyl lactate; polyol esters and pentaerythritol esters, fatty alcohols that are liquid at room temperature, with a branched and/or unsaturated carbon-based chain containing from 12 to 26 carbon atoms, for instance octyldodecanol, isostearyl alcohol, oleyl alcohol, 2-hexyldecanol, 2-butyloctanol and 2-undecylpentadecanol;

higher fatty acids such as oleic acid, linoleic acid or linolenic acid, and mixtures thereof.

The non-volatile silicone oils that may be used in the composition according to the invention may be nonvolatile polydimethylsiloxanes (PDMSs), polydimethylsiloxanes comprising alkyl or alkoxy groups, that are pendent and/or at the end of a silicone chain, the groups each containing from 2 to 24 carbon atoms, phenyl silicones, for instance phenyl trimethicones, phenyl dimethicones, phenyltrimethylsiloxydiphenylsiloxanes, diphenyl dimethicones, diphenylmethyldiphenyltrisiloxanes, and mixtures thereof.

For the purposes of the invention, the term "volatile oil" means any oil that is capable of evaporating on contact with the skin, at room temperature and atmospheric pressure. The volatile oils of the invention are volatile cosmetic oils, which are liquid at room temperature, having a nonzero vapour pressure, at room temperature and atmospheric pressure, ranging in particular from 0.13 Pa to 40 000 Pa (0.001 to 300 mmHg) and preferably ranging from 1.3 Pa to 1300 Pa (0.01 to 10 mmHg).

The volatile hydrocarbon-based oils may be chosen from hydrocarbon-based oils containing from 8 to 16 carbon atoms, and especially branched $C_8$-$C_{16}$ alkanes such as $C_8$-$C_{16}$ isoalkanes of petroleum origin (also known as isoparaffins), for instance isododecane (also known as 2,2,4,4,6-pentamethylheptane), isodecane, isohexadecane and, for example, the oils sold under the trade names Isopar® or Permethyl®.

Volatile oils that may also be used include volatile silicones, for instance volatile linear or cyclic silicone oils, especially those with a viscosity ≤5 centistokes ($5 \times 10^{-6}$ m²/s), and especially containing from 2 to 10 silicon atoms and preferably from 2 to 7 silicon atoms, these silicones optionally comprising alkyl or alkoxy groups containing from 1 to 10 carbon atoms. As volatile silicone oil that may be used in the invention, mention may be made in particular of octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

The oil may be present in the composition in a content ranging from 5% to 95% by weight and preferably ranging from 10% to 80% by weight relative to the total weight of the composition.

The composition may comprise water in particular in a mass content ranging from 5% to 90% and preferably ranging from 20% to 80% relative to the total mass of the composition.

The composition may also comprise conventional cosmetic additives chosen from film-forming polymers, waxes, pasty compounds, thickeners, surfactants, fragrances, preserving agents, sunscreens, fillers, dyestuffs, proteins, vitamins, provitamins, moisturizers, ceramides, pH regulators, and any other additive conventionally used in cosmetic compositions intended to be applied to keratin materials.

The coating may itself be capable of transferring onto human keratin materials.

The coating may be deposited onto the transfer surface before and/or after printing the coat of colouring ink. In one variant, the device comprises a first and a second cosmetic coating, borne by the transfer surface and located on either side of the coat of cosmetic ink. The first and the second cosmetic coatings in particular comprise different compositions.

The first and/or the second cosmetic coating may be coloured. The coating is, for example, coloured a colour that is difficult to print, for example white or black, or a colour close to the flesh tone of the skin to be made up, such as a flesh colour.

As a variant, the coating is not itself coloured.

At least one from among the first and second cosmetic coatings may be colourless.

The first and/or the second cosmetic coating is obtained, for example, from a composition chosen from a foundation, a lip gloss, a lip balm, a lipstick and an eyeshadow.

The coating may be a skincare product.

In one example, the colouring ink integrated into the coating is capable of transferring onto keratin materials without addition of an intermediary fluid compound, especially a liquid. In other words, the colouring ink may transfer onto the keratin materials by simple contact of the area intended to be made up with the said colouring ink, without it being necessary to apply an intermediary liquid intended to improve the transfer of the ink, as in the case of decal transfers.

Assemblies

According to another of its aspects, the present invention relates to a cosmetic assembly comprising, in the same case, a plurality of devices according to the invention, the devices differing by the chemical nature of the colouring ink they bear and/or by the pattern thereby formed and/or by the coating deposited on the transfer surface and/or by the form of the transfer surface intended to engage with the keratin materials.

The devices may differ by the form and/or the composition of the substrate, in particular the transfer surface intended to engage with the keratin materials.

The devices may differ by the chemical nature of the colouring ink they bear and/or by the pattern thereby formed.

The assembly may comprise one or more ink cartridges and substrate deformation means.

The assembly may also comprise a suitable printer.

When an intermediary compound that is useful for fluidizing the transfer compound(s) is used, the intermediary compound may be added within the colouring ink to the transfer compound(s) after printing.

The intermediary compound may be added, within the colouring ink, to the transfer compound(s) by any known means, especially by spraying.

The intermediary compound is preferably added to the transfer compound(s) before the application of the colouring ink to the keratin materials, while the colouring ink is still borne by the transfer surface.

In one embodiment example, the colouring ink is brought to a temperature of between 30° C. and 60° C. before being applied to the keratin materials. As a variant, the colouring ink is brought to a temperature of between 30° C. and 60° C. while it is in contact with the area of the keratin materials intended to be coated with the colouring ink.

When the colouring ink is intended to be brought to a temperature of between 30° C. and 60° C. prior to its application, the colouring ink brought to this temperature may be applied to the nails so as to produce a makeup result thereon by transfer.

When the transfer surface is detachable from a part of the substrate, the user can first detach the transfer surface from the rest of the substrate and then apply by transfer onto the keratin materials the colouring ink present on the transfer surface thus detached.

The colouring ink may be brought to a temperature of between 30° C. and 60° C. by being placed close to a heating member. As a variant, the colouring ink obtained just after printing may already be at such a temperature; the user can then apply to the keratin materials the colouring ink at this temperature, before it cools.

According to yet another aspect, the present invention relates to a kit for manufacturing a device according to the invention as described previously.

The kit may comprise, in the same packaging:
a) a printer cartridge containing at least one cosmetic colouring ink,
   a cosmetic composition comprising an oil that is capable of transferring onto the keratin materials, the composition being contained in a packaging assembly,
b) a substrate having at least one transfer surface intended to receive a coating of the composition and a coat of colouring ink printed using a digital printer.

The composition packaging assembly is, in a known manner, any packaging that is suitable for storing cosmetic compositions (especially a bottle, tube, spray bottle or aerosol bottle).

The invention may be understood more clearly on reading the following description and on examining the attached drawing, in which:

FIGS. 1 to 3 represent different steps of a makeup process according to a first mode of the invention, FIGS. 4 and 5 represent different steps of a makeup process according to a second mode of the invention, and FIGS. 6 and 7 illustrate a variant of the makeup process according to the invention.

FIGS. 1 to 3 show a makeup device 1 according to the invention, comprising a substrate 2 made of a flexible and deformable material, the front face of which constitutes a transfer surface 3 intended to receive a coat of cosmetic colouring ink 4, to produce a makeup result by transfer.

To deposit the coat of colouring ink 4 onto the transfer surface 3, use is made of a digital printer, which deposits the ink dots in correspondence with the pixels of an image to be reproduced.

A pattern 40 representing in negative the image to be reproduced is printed directly onto the transfer surface 3. FIG. 1 shows the device 1 after printing, once removed from the printer, the transfer surface 3 bearing a coat of cosmetic ink 4.

All or part of the area of the transfer surface 3 superposed on the coat 4 is preferably smooth and has a roughness of less than or equal to 1 mm, especially between 1 and 100 µm and preferably less than or equal to 50 µm. The roughness is measured using a roughness meter, the tip of which has a radius of curvature of 10 mm, and the force of which, applied to the material to be characterized, is 6 mN.

The coat of colouring ink 4 may form any type of pattern, for example in the form of a heart and of text as illustrated. The pattern may consist of several inks.

The substrate 2 may bear an indication 7, for example formed by printing, for providing information regarding a recommended positioning for the makeup, or providing information regarding the nature of the keratin materials intended to be made up with the ink 4, or the like.

A coating 6 is then applied as illustrated in FIGS. 2 and 3. The coating is, for example, coloured and corresponds to the application of a foundation.

The invention is not limited to a type of coating. The coating may be of any type known for the cosmetic treatment of, in particular for making up, the body or the lips.

In this example, the cosmetic coating 6 covers the coat of ink 4, being totally superposed on the pattern of the coat of ink 4. As shown by the section of FIG. 3, the coating 6 integrates the ink of the coat 4 while at the same time preserving the pattern 40. To help this incorporation of the coat of ink 4 into the coating 6, the user can optionally make rectifications in order, for example, to attenuate the edges.

Preferably, the substrate 2 has at least one non-opaque area 5, which is preferably transparent or translucent, and which may totally or partly be superposed with the coat of colouring ink 4 and the coating 6. The transparent area 5 allows the user to see through the substrate 2 and thus to visualize the surface to be made up through the device 1 when this device is superposed on the said surface.

All of 4 and of the coating 6 may, as illustrated, be superposed on the transparent area 5. In one variant, not shown, only part of the coating and/or of the coat of colouring ink is superposed on the transparent area 5.

The substrate 2 may be made of a transparent material. The transparent area 5 then extends over the entire surface of the substrate 2.

The substrate 2 may bear an indication 7, for example a print, for providing information regarding a recommended positioning for the makeup, for example a reproduction, the right way around and at reduced scale, of the pattern to be transferred, as illustrated, or the nature of the keratin materials intended to be made up with the colouring ink 4, or the like, and may also provide information regarding the colour and/or pattern reference.

The substrate 2 is preferably made of a flexible material. As a variant, the substrate 2 is made of a rigid or semi-rigid material.

The device 1 is then brought close to the area of skin P to be made up, which is preferably dry, so as to place the coat of colouring ink 4 and the coating 6 simultaneously in contact with the area of skin P to be made up, and the user then applies a pressure allowing the colouring ink 4 and the coating 6 to be transferred onto the area to be made up P. During the contact with the keratin materials, the substrate 2 is preferably not moved sideways so as not to affect the appearance of the transferred pattern.

The substrate 2 bearing the transfer surface 3 is removed. The makeup result obtained combines the pattern corresponding to the ink and the coating. Good precision of the pattern is maintained, by means of printing, without it being impaired by the coating.

In one variant, not shown, a coat of ink forming coloured patterns is printed on a transfer surface, coating is applied to a transfer surface using a lip gloss, a lip balm or a lipstick. The transfer surface is then placed on the area of the lips. A standard makeup result is obtained in a single gesture with the coating composition combined with the patterns.

FIGS. 4 and 5 schematically show various steps of another embodiment of a makeup process according to the invention.

FIG. 4 shows a transfer surface 3 of a substrate 2 onto which has been applied a coating 6, for example a foundation coat, to which is optionally added an additional colour coat. It is possible to perform one and then the other, or vice versa.

To deposit a coat of colouring ink 4 onto the transfer surface 3 covered with the coating 6, use is made of a digital printer, which deposits the ink dots in correspondence with the pixels of an image to be reproduced. It is possible to modify at will one's patterns by referring to a library of patterns, or even by constructing one's own patterns (colour, shape, distribution).

The device 1 is then brought close to the area of skin P to be made up, which is for example dry, so as to place the coat of colouring ink 4 and the coating 6 simultaneously in contact with the area of skin P to be made up, and the user then applies a pressure allowing the colouring ink 4 and the coating 6 to be transferred onto the area to be made up P. During the contact with the keratin materials, the substrate 2 is preferably not moved sideways so as not to affect the appearance of the transferred pattern.

The substrate 2 bearing the transfer surface 3 is removed. Skin defects are masked by means of the foundation. The patterns produced by the transferred coat of ink are also detected. Although positioned between the area P of skin and the coating 6 of foundation, the patterns are visible. Thus, a visual result that is pleasant since it is not too homogeneous is obtained.

The makeup process is very practical to perform and the relative positioning of the coating and of the coat of ink is done successfully since it is performed in a single gesture.

EXAMPLES

Example 1

This Example Corresponds to FIGS. 6 and 7

A coating 6 of foundation having the composition described below is deposited on a substrate 2 consisting of a plastic sheet of transparent type for a printer. The coating is left to dry.

| Foundation composition | |
|---|---|
| Ingredients | (weight %) |
| Magnesium sulfate | 1.50 |
| Distearyldimethylammonium-modified hectorite (Bentone 38 VCG from Elementis) | 1 |
| Titanium dioxide | 21.20 |
| Iron oxides | 3.8 |
| Sodium carboxymethylcellulose (Blanose ® 7M8SF from Ashland) | 0.50 |
| Cyclopentasiloxane | 15.30 |
| Polyglyceryl-4 isostearate cetyl PEG/PPG-10/1 hexyl laurate (Abil WE 09 from Evonik Goldschmidt) | 9 |
| Polydimethylsiloxane (viscosity: 5 cst) (Xiameter PMX-200 Silicone Fluid 5 cs from Dow Corning) | 6.60 |
| Glycerol | 5 |
| Pentylene glycol | 3 |
| Water | qs 100 |

The next day, a coat of ink 4 representing a series of small grains is printed as illustrated in FIG. 6. A Canon Pixma IP100 inkjet printer is used, equipped with Canon printer cartridges containing four inks corresponding to the formulations given in the table below.

| | Yellow I | Magenta I | Cyan I | Black I |
|---|---|---|---|---|
| Dye | 1% | 1% | 1% | 1% |
| Isopropanol | 8% | 8% | 8% | 8% |
| Ethanol | 10% | 10% | 10% | 10% |
| Water | qs 100% | qs 100% | qs 100% | qs 100% |

The substrate 2 is then placed on the arm so as to have contact between the coating 6, the coat of ink 4 and the area P of skin to be made up.

When the sheet is removed, it is found that the foundation is transferred along with the small grains and that the small grains are entirely visible, despite the covering power of the foundation, as shown in FIG. 7.

Example 2

This example corresponds to FIGS. 1 to 3.

A coat of ink 4 is printed on the transfer surface 3 of a substrate 2 similar to the plastic sheet of Example 1.

The transfer surface 2 is then covered with a coating 6 of foundation of Example 1.

The whole is then applied to the skin, the coating 6 and the coat of ink 4 being in contact with the area P to be treated.

The substrate is removed. The makeup result obtained combines the pattern and the foundation. The pattern is integrated into the foundation, which affords a certain amount of discretion. Good precision of the pattern is maintained, by means of printing, without it being impaired by the foundation.

The invention claimed is:

1. A process for making up an area of human keratin materials using a makeup device comprising
   a substrate having at least one transfer surface, and
   a coat of cosmetic colouring ink borne by the transfer surface and obtained by printing, using at least one digital printer, and a first and a second cosmetic coating of a cosmetic composition comprising an oil borne by the transfer surface and located on either side of the coat of cosmetic colouring ink, the first cosmetic coating being at least partially superposed on the coat of ink and laying above the coat of ink, the coat of cosmetic colouring ink is directly deposited onto the second cosmetic coating and the first cosmetic coating is spaced apart from the transfer surface with portions of the coat of cosmetic colouring ink positioned there between, the process comprising the step of simultaneously transferring onto the area to be made up all or part of the coat of ink and all or part of the first cosmetic coating superposed thereon.

2. The process according to claim 1, also comprising the step consisting in moving the transfer surface away from the area of the human keratin materials after the coat of ink and the first cosmetic coating have been transferred.

3. The process according to claim 1, the colouring ink and/or the first cosmetic coating not being entirely dry at the time of transfer.

4. The process according to claim 1, the cosmetic composition comprising the oil being anhydrous or being an emulsion.

5. The process according to claim 1, the cosmetic composition comprising in the oil in an amount by mass ranging from 5% to 95% relative to the total mass of the composition.

6. The process according to claim 1, the cosmetic composition comprising the oil and at least one cosmetic additive chosen from film-forming polymers, waxes, pasty compounds, thickeners, surfactants, fragrances, preserving agents, sunscreens, fillers, dyestuffs, proteins, vitamins, provitamins, moisturizers, ceramides and pH regulators.

7. The process according to claim 1, the ink being aqueous.

8. A process for manufacturing a transfer device for making up human keratin materials, comprising a substrate having at least one transfer surface,
comprising the following steps:
printing at least one coat of at least one cosmetic colouring ink on the transfer surface using at least one digital printer,
applying at least first and second cosmetic composition comprising an oil to the transfer surface to form a coating on either side of the cost of cosmetic colouring ink,
the first cosmetic coating being at least partially superposed on the coat of colouring ink,
the coat of colouring ink being deposited directly onto the second cosmetic coating and the first cosmetic coating is spaced apart from the transfer surface with portions of the coat of colouring ink positioned there between,
the coat of colouring ink and the first cosmetic coating being intended to be transferred simultaneously onto the keratin materials so as to obtain a makeup result on the keratin materials.

9. The process according to claim 8, the coat of colouring ink being printed in a predefined pattern.

10. The process according to claim 8, the printing of the coat of ink being performed on the transfer surface already partly covered with the second cosmetic coating.

11. A transfer device for making up human keratin materials, comprising:
a substrate having at least one transfer surface,
a coat of cosmetic colouring ink borne by the transfer surface and obtained by printing, using at least one digital printer, and
a first and a second cosmetic coating comprising an oil borne by the transfer surface and located on either side of the coat of cosmetic colouring ink,
the first cosmetic coating laying above the coat of ink, at least partially superposed on the coat of ink,
the coat of cosmetic colouring ink is directly deposited onto the second cosmetic coating and the first cosmetic coating is spaced apart from the transfer surface with portions of the coat of cosmetic colouring ink positioned there between,
the coat of colouring ink and the first cosmetic coating being intended to be applied to the keratin materials so as to obtain, by transfer, a makeup result on the keratin materials.

12. The device according to claim 11, the first and/or the second cosmetic coating being obtained using a composition chosen from a foundation, a lip gloss, a lipstick and a skincare product.

13. The device according to claim 11, the first and/or the second cosmetic coating being coloured.

14. The device according to claim 11, at least one from among the first and second cosmetic coatings being colourless.

15. The device according to claim 11, the transfer surface being defined by all or part of: the outer surface of an applicator roller, the surface of an applicator pad, an element in sheet form, a patch, the surface of a porous foam, a sponge, a wipe.

16. The device according to claim 11, the substrate comprising an indication regarding the nature of the keratin materials intended to be made up with the colouring ink and/or the substrate comprising at least one translucent or transparent area.

17. A cosmetic assembly comprising, in the same case, a plurality of different devices, each being according to claim 11, the devices differing by the chemical nature of the coat of colouring ink they bear and/or by the pattern thereby formed and/or by the coating deposited on the transfer surface and/or by the form of the transfer surface intended to engage with the keratin materials.

* * * * *